(12) United States Patent
Sun et al.

(10) Patent No.: US 11,452,478 B2
(45) Date of Patent: Sep. 27, 2022

(54) SYSTEM AND METHOD FOR DETECTING ALZHEIMER'S DISEASE

(71) Applicant: Nation Taiwan University, Taipei (TW)

(72) Inventors: Chi-Kuang Sun, Taipei (TW); Sandeep Chakraborty, Taipei (TW)

(73) Assignee: Nation Taiwan University, Taipei (TW)

( * ) Notice: Subject to any disclaimer, the term of this patent is extended or adjusted under 35 U.S.C. 154(b) by 335 days.

(21) Appl. No.: 16/874,555

(22) Filed: May 14, 2020

(65) Prior Publication Data
US 2021/0353207 A1    Nov. 18, 2021

(51) Int. Cl.
*A61B 5/00*      (2006.01)
*G02F 1/37*      (2006.01)
*G06T 7/00*      (2017.01)
*G02F 1/35*      (2006.01)

(52) U.S. Cl.
CPC .............. *A61B 5/4088* (2013.01); *G02F 1/37* (2013.01); *G06T 7/0012* (2013.01); *G02F 1/354* (2021.01); *G06T 2207/10024* (2013.01); *G06T 2207/10056* (2013.01); *G06T 2207/20212* (2013.01); *G06T 2207/30016* (2013.01)

(58) Field of Classification Search
CPC ....... A61B 5/4088; A61B 5/0071; G02F 1/37; G02F 1/354; G06T 7/0012; G06T 2207/10024; G06T 2207/10056; G06T 2207/20212; G06T 2207/30016; G06T 5/50; G06T 2207/20221; G06T 2207/30024
See application file for complete search history.

(56) References Cited

U.S. PATENT DOCUMENTS

2018/0180550 A1* 6/2018 Franjic ................. G01N 21/474

OTHER PUBLICATIONS

Wang, Shu "Label-free multiphoton imaging of B-amyloid plaques in Alzheimer's disease mouse models" Neurophotonics (Year: 2019).*
Chakraborty, Sandeep, et al., "Additive-Color Multi-Harmonic Generation Microscopy for Simultaneous Label-Free Differentiation of Plaques, Tangles, and Neuronal Axons", Biomedical Optics Express, Feb. 2020, vol. 11, No. 2, pp. 571-585.

* cited by examiner

*Primary Examiner* — Emily C Terrell
*Assistant Examiner* — Molly Wilburn
(74) *Attorney, Agent, or Firm* — Millikin Intellectual Property Law, PLLC

(57) ABSTRACT

The present invention provides a system for detecting whether a subject having a target suffers from an Alzheimer's disease. The system includes a multi-harmonic generation microscope and a processor. The multi-harmonic generation microscope images the target by a second harmonic generation (SHG) and a third harmonic generation (THG) to respectively obtain an SHG image and a THG image. The processor couples to the multi-harmonic generation microscope and configures to add a first color to the SHG image and a second color to the THG image to respectively obtain a color-added SHG image and a color-added THG image, and combine the color-added SHG image and the color-added THG image to obtain a combined image, wherein the combined image is used to determine whether the subject suffers from the Alzheimer's disease.

20 Claims, 6 Drawing Sheets
(2 of 6 Drawing Sheet(s) Filed in Color)

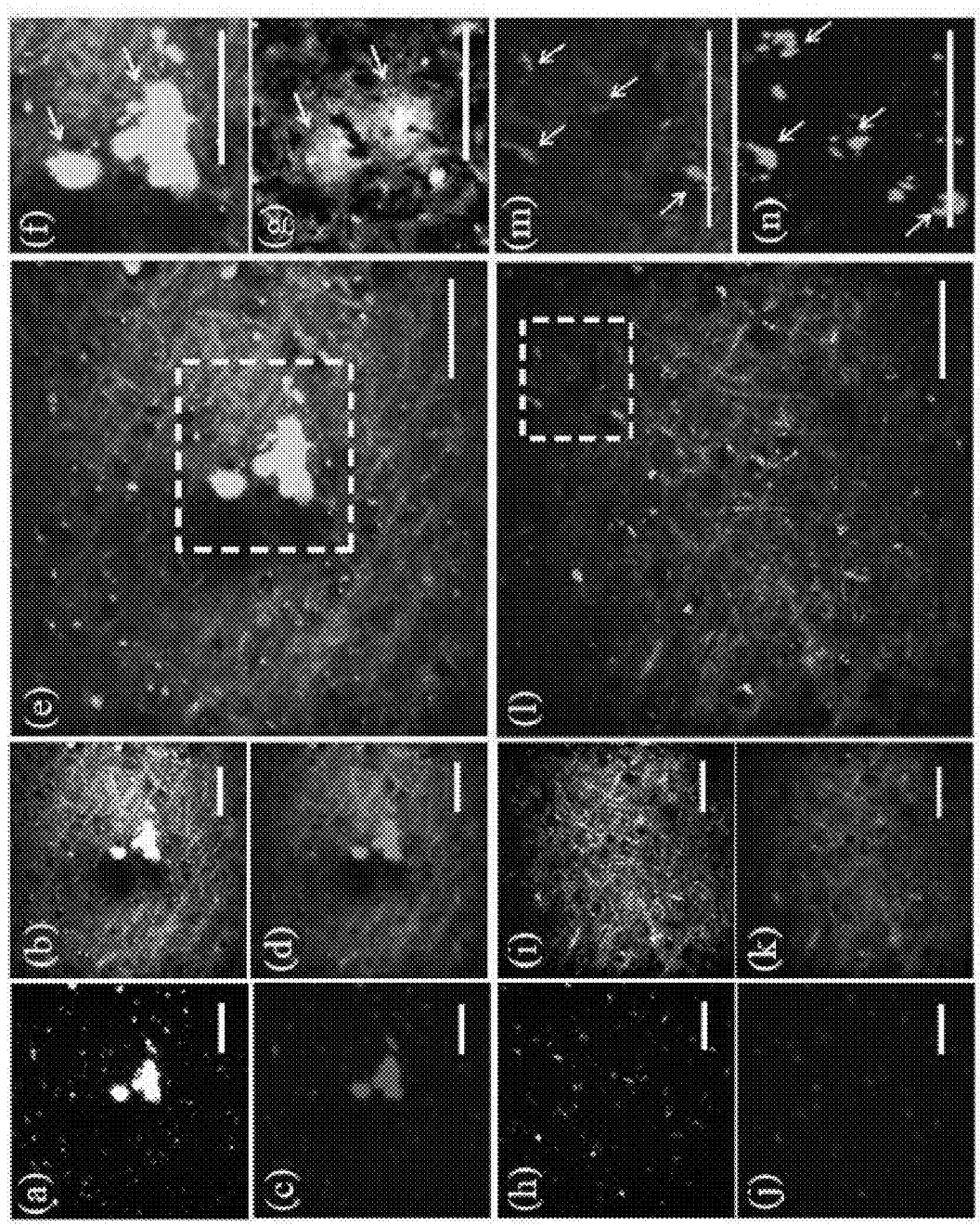
Figs. 3(a)~3(n)

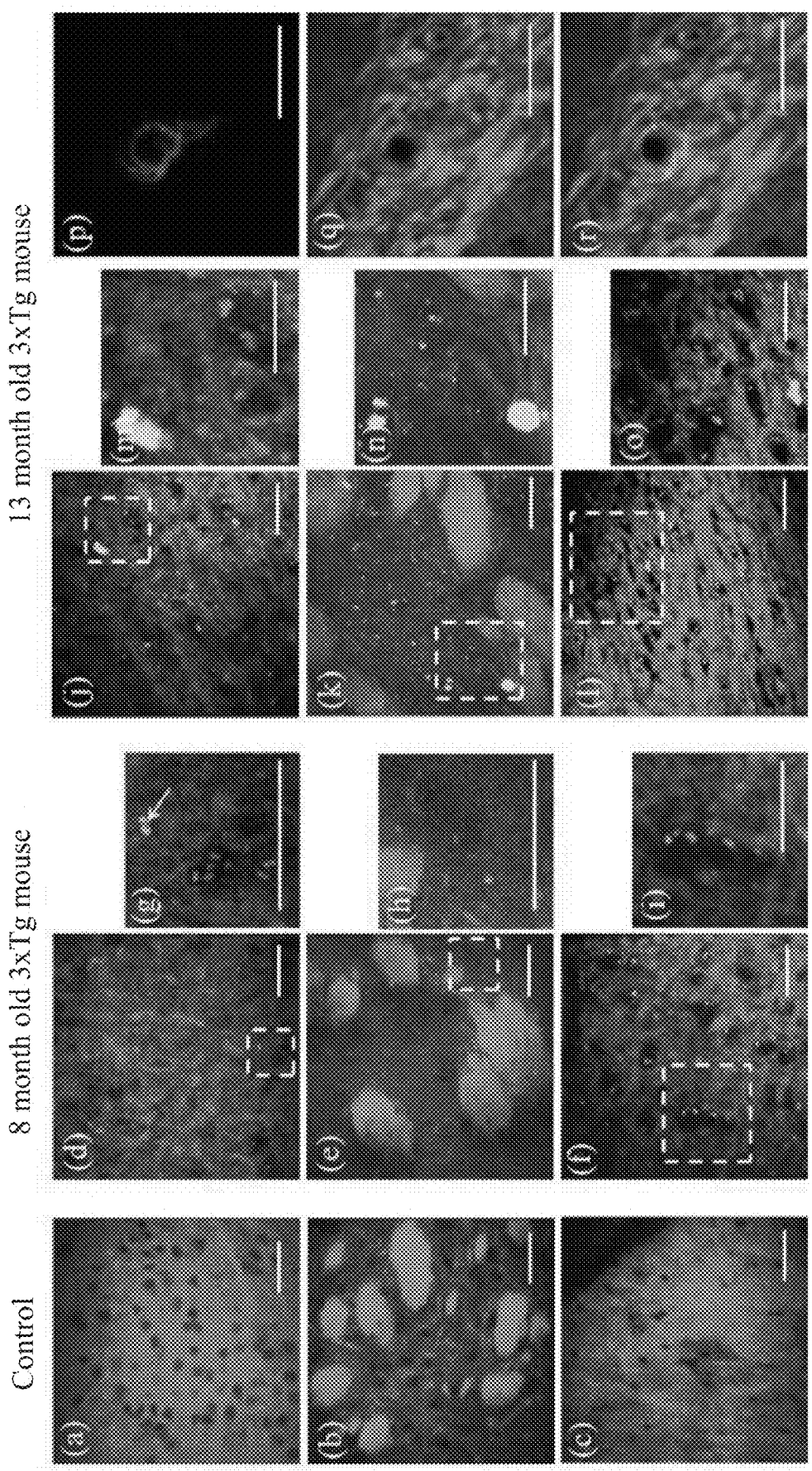
Figs. 5(a)~5(r)

SYSTEM AND METHOD FOR DETECTING ALZHEIMER'S DISEASE

FIELD OF THE INVENTION

The present invention is related to a device and a method for detecting whether a subject suffers from Alzheimer's disease. Particularly, the present invention is related to a device and a method for detecting whether a subject suffers from Alzheimer's disease using a second harmonic generation (SHG) image and a third harmonic generation (THG) image.

BACKGROUND OF THE INVENTION

Multicolor fluorescence imaging has been widely used by neuroscientists to simultaneously observe different neuropathological features of the brain. However, these optical modalities rely on exogenous labeling.

In our nervous system, neurons construct complex networks, forming connectomes with thousands of synapses possibly overlapping in a tiny volume. Analyzing and understanding such complex systems in time and space need sophisticated visualization tools which can provide a display distinguishing individual neuropathological components. And perhaps the most useful visual modality for such purposes is color, considering our vision can process multivariate information present in a complex visual field.

In this situation, multicolor fluorescence imaging using multiple probes has been developed and provides an important capability of fluorescence microscopy for in vivo optical imaging. Among the techniques of exogenous fluorescence labeling of neurological structures, the brainbow strategy has been widely utilized for genetic cell-labeling with primarily red, green and blue fluorescent proteins (FPs). The technique is based on the fact that the colors red, green, and blue (RGB) can combine to generate hundreds of different hues. Brainbow can achieve such effects by expressing different ratio of FPs within cells. The color combinations are unique in a category of cells, and can be used as cellular identification tags under a light microscope. Although over the years, brainbow technologies have found firm places in the genetic toolbox of neuroscientists, the major concern regarding its utility in clinical pathology practice, to study neurodegenerative disorders like Alzheimer's disease (AD), involves the use of exogenous FPs along with color imbalance and discrimination.

Moreover, in clinical practice, the gold standard for definitive confirmation and diagnosis of AD comes from the histopathology and/or immunohistochemical staining procedures of AD brain tissues to reveal its neuropathological hallmarks. However, these protocols require long fixation time, tedious embedding and staining procedures as well as microscopic analysis which make the sample analysis a severely time-consuming process. Considering such a scenario, there is an urgent need of a new technique which can provide diagnostically relevant information, quickly and reliably through a visual display of the AD disease hallmarks in a level-free slide-free approach in clinical settings.

Pathologically, AD is associated with the aggregation of insoluble forms of amyloid-$\beta$ (A$\beta$) in plaques (A$\beta$ plaques) in extracellular space and microtubule protein tau in neurofibrillary tangles (NFT) in neurons. In the development of label-free tools for AD pathology, autofluorescence of the diseased brain tissues was evaluated and had shown that autofluorescence can detect senile plaques and NFT in the brain tissues from human subjects. Both the senile plaques and NFT generate blue emissions (plaques at >430 nm; while NFT at about 460 nm) when excited with ultraviolet light, and hence this limits the simultaneous differentiation of these two features in brain tissues. In addition, these studies were also limited to wide-field, or confocal microscopy on superficial areas, or thinly sliced sections. Recently, hyperspectral Raman imaging was used for the identification of neurotic plaques and NFT along with water, lipids, and proteins. However, the technique is severely limited by its low spatial resolution, image acquisition speeds, and most importantly it did not provide a way to distinguish distinctly the plaques and NFTs from other lipid or protein structures. On the other hand, coherent anti-stokes Raman scattering (CARS) imaging was only able to see the lipids associated with the plaques, and showed no evidence regarding NFT. In general, these techniques depend on the differences in the vibrational spectra, and are time consuming due to their requirements to compare the measured with a library of reference spectra. Recently, although a polarization sensitive optical coherence tomography (OCT) has also been successful in identifying only plaques, the very low spatial resolutions thereof causes the polarization sensitive OCT to be unable to provide information regarding axonal networks. No reported work has been published regarding OCT in identifying NFT. Most importantly, all these techniques have failed to provide a visual display, like that of the brainbow strategy, to discriminate between the different neuropathological hallmarks of the AD simultaneously in a single image field-of-view with ultrahigh resolution.

It is therefore the Applicant's attempt to deal with the above situation encountered in the prior art.

SUMMARY OF THE INVENTION

The present invention has the potential of concurrently using the label-free nonlinear optical microscopy techniques: the second and third harmonic generation (SHG and THG) microscopy to provide a dual contrast additive multicolor mechanism to display the various structural features of AD brain tissue simultaneously with different hues. By treating the third harmonic generation (THG) and the second harmonic generation (SHG) as two primary colors, the present invention indicates different additive colors between neuronal axons, A$\beta$ plaques and NFT. The additive color multi-harmonics of the present can approach as a label-free slide-free multicolor imaging platform for differential visualization of AD hallmark structures based on an excitation wavelength in the optical window of the brain.

In accordance with another aspect of the present disclosure, a system for detecting whether a subject having a target suffers from an Alzheimer's disease is disclosed. The system includes: a multi-harmonic generation microscope imaging the target by a second harmonic generation (SHG) and a third harmonic generation (THG) to respectively obtain an SHG image and a THG image; and a processor coupled to the multi-harmonic generation microscope and configured to: add a first color to the SHG image and a second color to the THG image to respectively obtain a color-added SHG image and a color-added THG image; and combine the color-added SHG image and the color-added THG image to obtain a combined image, wherein the combined image is used to determine whether the subject suffers from Alzheimer's disease.

In accordance with one more aspect of the present disclosure, a method for detecting whether a subject having a target suffers from an Alzheimer's disease is disclosed. The method includes steps of: imaging the target by a second harmonic generation (SHG) and a third harmonic generation (THG) via a multi-harmonic generation microscope to obtain an SHG image and a THG image; adding a first color for the SHG image and a second color for the THG image via a processor to obtain a color-added SHG image and a color-added THG image; combining the color-added SHG image and the color-added THG image via the processor to obtain a combined image; and determining whether the subject suffers from Alzheimer's disease according to the combined image of the target.

In accordance with one more aspect of the present disclosure, a method for detecting a characteristic of a neural structure is provided. The method includes steps of: imaging a target by a second harmonic generation (SHG) and a third harmonic generation (THG) via a multi-harmonic generation microscope to obtain an SHG image and a THG image respectively; processing the SHG image and the THG image with two different image processing treatments to obtain a processed SHG image and a processed THG image respectively, wherein a combination of the two different image processing treatments highlights the characteristic; and combining the processed SHG image and the processed THG image to obtain a combined image to determine the characteristic.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Other objectives, advantages and efficacies of the present invention will be described in detail below taken from the preferred embodiments with reference to the accompanying drawings.

FIGS. 3(a) and 3(b) respectively shows the SHG image and the THG of the cortex with gray labeled image.

FIGS. 3(c) and 3(d) respectively shows the red color added SHG image of FIG. 3(a) and the green color added THG image of FIG. 3(b).

FIG. 3(e) shows the combined image of the red color added SHG image in FIG. 3(c) and the green color added THG image in FIG. 3(d).

FIG. 3(f) is an enlarged view of the dotted box region in FIG. 3(e).

FIG. 3(g) shows is an immunohistochemical staining result of the Aβ plaques at the corresponding region in FIG. 3(f).

FIGS. 3(h) and 3(i) respectively shows the SHG image and the THG of another region of the cortex with gray labeled image.

FIGS. 3(j) and 3(k) respectively shows the red color added SHG image of FIG. 3(h) and the green color added THG image of FIG. 3(i).

FIG. 3(l) shows the combined image of the red color added SHG image in FIG. 3(j) and the green color added THG image in FIG. 3(k).

FIG. 3(m) is an enlarged view of the dotted box region in FIG. 3(l).

FIG. 3(n) shows is an immunohistochemical staining result of the NFT at the corresponding region in FIG. 3(m).

FIGS. 5(a), 5(b) and 5(c) respectively show the images of the cortex, the striatum and the hippocampal layer of the normal brain tissue in C57BL/6 mouse using the additive color multi-harmonic generation microscopy.

FIGS. 5(d), 5(e) and 5(f) respectively show the images of the cortex, the striatum and the hippocampal layer of the brain tissue in 8 month old 3xTg mouse using the additive color multi-harmonic generation microscopy.

FIGS. 5(g), 5(h) and 5(i) are enlarged views of the dotted box region in FIGS. 5(d), 5(e) and 5(f), respectively.

FIGS. 5(j), 5(k) and 5(l) respectively show the images of the cortex, the striatum and the hippocampal layer of the AD brain tissue in 13 month old 3xTg mouse using the additive color multi-harmonic generation microscopy.

FIGS. 5(m), 5(n) and 5(o) are enlarged views of the dotted box region in FIGS. 5(j), 5(k) and 5(l), respectively.

FIGS. 5(p), 5(q) and 5(r) respectively show red color added SHG image, the green color added THG image, and the combined image of the flame-like NFT of the AD brain tissue in 13 month old 3xTg mice using the additive color multi-harmonic generation microscopy.

DETAILED DESCRIPTION OF THE PREFERRED EMBODIMENTS

Figure 1:
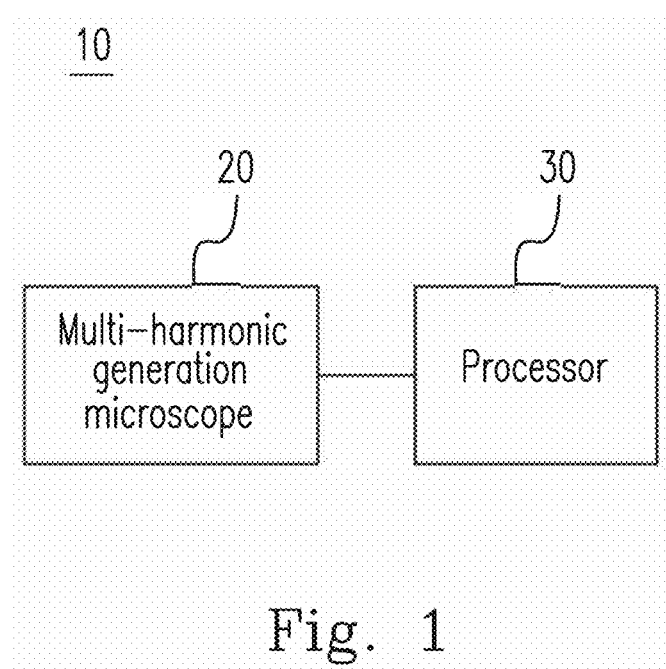
FIG. 1 shows a schematic diagram of the system for detecting whether a subject suffers from an Alzheimer's disease of the present invention.

The present invention will now be described more specifically with reference to the following embodiments. It is to be noted that the following descriptions of preferred embodiments of this invention are presented herein for purpose of illustration and description only; they are not intended to be exhaustive or to be limited to the precise form disclosed. In the preferred embodiments, the same reference numeral represents the same element in each embodiment.

Figure 2:
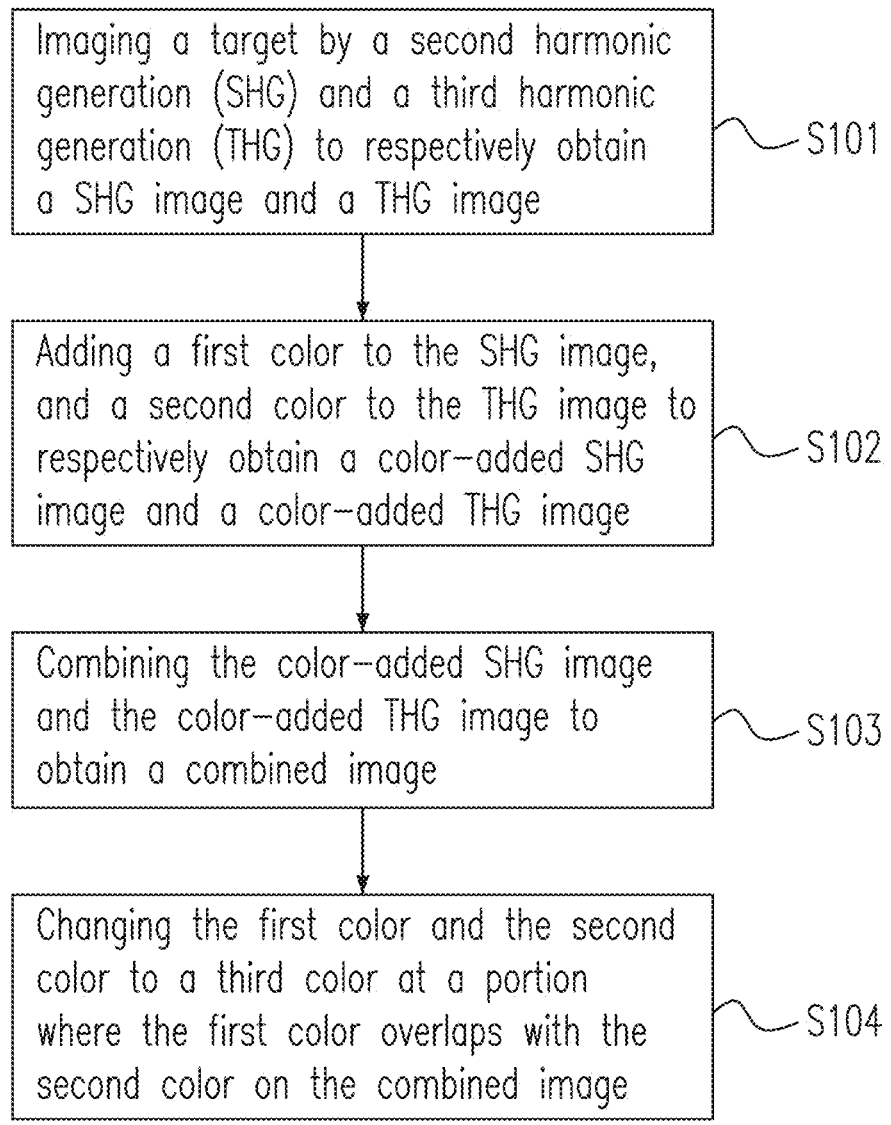
FIG. 2 shows a flowchart of the method for detecting whether a subject suffers from an Alzheimer's disease of the present invention.

Please refer to FIGS. 1 and 2, which are the system and the method for detecting whether a subject suffers from an Alzheimer's disease of the present invention. The system 10 the present invention is called additive color multi-harmonic generation microscopy, and includes a multi-harmonic generation microscope 20 and a processor 30.

The multi-harmonic generation microscope 20 involves a nonlinear coherent polarization process induced by inorganic or organic structures with specific physical properties, molecular arrangements and order. The multi-harmonic generation microscope 20 of the present invention has the combined modalities of second harmonic generation (SHG) and the third harmonic generation (THG). In the SHG process, two incident photons are converted into one photon with twice the energy and half the wavelength. In the THG process, three incident photons are converted into one photon with thrice the energy and one third of the wavelength. During the harmonic generation process, no excess energy is deposited in the organic structures, while no bleaching and phototoxicity effects are expected.

SHG relies on the second order non-linear susceptibility $\chi^{(2)}$ of the tissue and arises from well-organized non-centrosymmetric molecules such as collagen. Therefore, the beta sheet structures of Aβ plaques and NFT can provide strong SHG signals.

THG occurs at structural interfaces such as the spatial variation of third order non-linear susceptibility $\chi^{(3)}$ directly reflect the nature of molecules regardless of their higher order arrangement. In addition, the THG signal intensity also varies significantly with size and organization of the signal-originating structures at the micrometer scale, and thus depends on the focal volume of the imaging system. The molecules such as lipids have very high value of $\chi^{(3)}$ and consequently generate strong THG signals under 1200 nm excitation. The typical diameter of axons and dendrites ranges between 0.3 to 2 µm, and the axon structures are composed of lipids (myelin sheath). Hence, the axons and dendrites can provide strong THG signals. Similarly, the neural soma has diameter about 10-25 µm, thickness about 10-14 µm, and large nucleus. Considering the parameters (0.56 µm focal beam diameter and 0.32 µm lateral resolution) of the multi-harmonic generation microscope 20 for SHG, and the physical dimension and properties of soma, the THG signal will be extremely weak or nonexistent when the laser beam focuses on them. Therefore, the neuronal cell bodies will appear dark in the THG image.

According to above, the Aβ plaques and NFT will have different intensities of THG signal because of their varying size and organization. In advanced AD mice model, large plaque structures (5-50 µm) with inhomogeneous densely aggregated Aβ structural organization can be found everywhere in brain, and the Aβ plaques associate with lipid. Therefore, the Aβ plaques provide a stronger THG signal due to the non-linear increase in the forward to backward THG ratio. NFT is found as intercellular entity with smaller size and loosely bound aggregated structure tau protein, and hence, the NFT provides weak THG signals.

In the present invention, a target for the system 10 is a brain tissue of a subject, and the target can be imaged in vivo and in vitro. Please refer to FIGS. 1-2, the target was imaged in vitro using the SHG and the THG of the multi-harmonic generation microscope 20 to respectively obtain an SHG image and a THG image (Step 101), wherein the subject is mice. The SHG image and the THG image are gray labeled images. The SHG image and the THG image need to be processed with different image processing treatments for highlighting the characteristics of different structures. The different image processing treatments are that the processor 30 adds a first color to the SHG image and a second color to the THG image to respectively obtain a color-added SHG image and a color-added THG image (Step 102). For example, the SHG image is added red and the THG image is added green. Subsequently, the processor 30 combines the color-added SHG image and the color-added THG image to obtain a combined image (Step 103). When the first color overlaps with the second color on the combined image, the processor 30 changes the first color and the second color to a third color at the overlapped portion (Step 104). On the color-added SHG image and the color-added THG image, different structures have different intensities of the first color brightness and the second color brightness, and a color of the third color depend on the intensities of the first color brightness and the second color brightness. The color of the third color falls between the first color and the second color. For example, the red SHG image and the green THG image are combined to obtain the combined image. On the combined image, if the intensity of the red brightness is the same as that of the green brightness at the overlapped portion, the third color is yellow; and if the intensity of the red brightness is stronger than that of the green brightness at the overlapped portion, the third color is orange and/or apricot. The color of the third color falls between red and green. The colors of the first color, the second color and the third color can be altered according to a preference of a user.

In an embodiment of the present invention, because the Aβ plaques are strong on the SHG image and the THG image, the Aβ plaques will be showed in yellow on the combined image; because the NFT is strong on the SHG image and weak on the THG image, the NFT will be showed in more predominatly in red, and/or orange on the combined image; and because the axon and the dendrites are strong only on the THG image, the axon and the dendrites will be showed in green on the combined image. If there are yellow color, and at least one of red color and orange color on the combined image, it can be determined that the subject suffers from AD. Therefore, the system of the present invention can provide different colors for different characteristics of neural structures without labeling and sliding to quickly differentiate the hallmarks of AD to determine AD.

Experiment Examples

Demonstrating the Effect of the System of the Present Invention

In the present invention, 3xTg AD mice model was used to demonstrate that the system can discern the neuropathology of AD. Fresh brain tissues from a 13 month old 3xTg AD mouse were used as the sample, and the results are shown in FIGS. 3(a)-3(e) and 3(h)-3(l). In a first example, please refer to FIGS. 3(a)-3(b), which respectively shows the SHG image and the THG image of the cortex with gray labeled images. For distinguishing different characteristics of different structures, red is added to the SHG image and green is added to the THG image, as shown in FIGS. 3(c)-3(d), respectively. When FIGS. 3(c) and 3(d) are combined, the overlap portions are showed in yellow or different hues of yellow, as shown in FIG. 3(e), wherein the green color is axons, the yellow color is a big-clump-like structure, and the red color is intraneuronal. FIG. 3(f) is an enlarged view of the dotted box region in FIG. 3(e).

To further observe other small red specks, the other area of the cortex was imaged, as shown in FIGS. 3(h)-3(l). FIGS. 3(h) and 3(i) respectively shows the gray labeled images of the SHG image and the THG image. The color added images of the SHG image and the THG image are respectively shown in FIGS. 3(j) and 3(k), and the combined image of FIGS. 3(j) and 3(k) is shown in FIG. 3(l). In FIG. 3(l), it can be seen that the intraneuronal structures appear mostly as red; red with some places at different hues of yellow (orange). FIG. 3(m) is an enlarged view of the dotted box region in FIG. 3(l).

To understand the contrast origin of the SHG and THG related to the bright-yellow colored big clump extraneuronal structure and the intraneuronal red colored structures, the AD brain tissues were stained with anti-β-amyloid to identify the plaques while the antibody PHF-1 was used for NFT using immunohistochemical (IHC) staining to avoid non-specific fluorescent imaging, and the result for Aβ plaques is shown in FIG. 3(g) and the result for NFT is shown in FIG. 3(n). The immunohistochemical stained imaging are shown in cyan hot color. Comparing the IHC staining result for Aβ plaques (FIG. 3(g)) with the multi-harmonic generation microscope image (FIG. 3(f)), it can be seen that there are similar characteristics at the arrow regions between FIGS. 3(f) and 3(g), and FIGS. 3(m) and 3(n). Specifically, the yellow color in FIG. 3(e) is the Aβ plaques which provide strong contrast for both THG and SHG, and the red and red-orange color in FIG. 3(l) is the NFT. Consequently, the system of the present invention can enable one to visualize concurrently different hallmark structures of AD pathology depending on color.

Figure 4A:
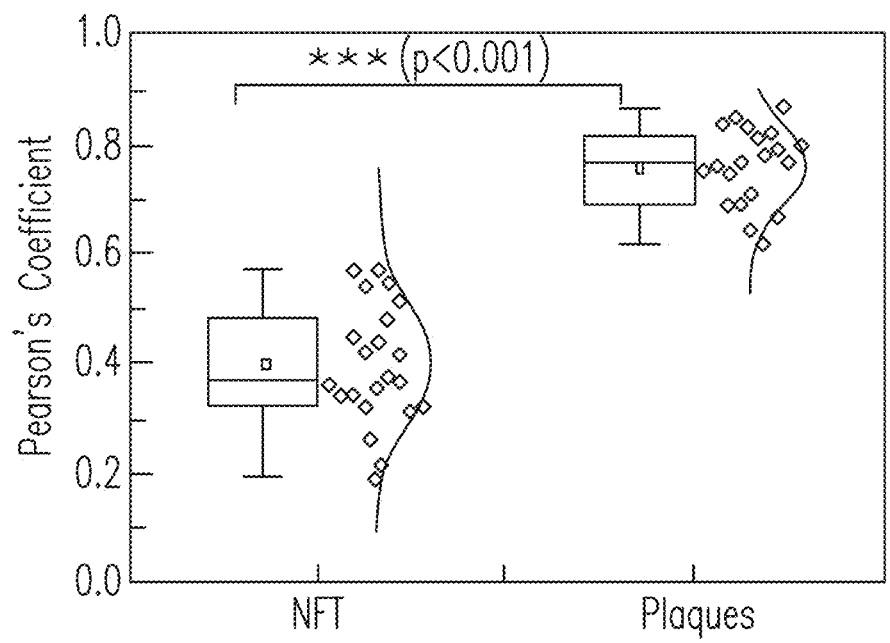
FIG. 4(a) shows the result of comparison of the Pearson's correlation coefficient between THG and SHG.

Quantitative Evaluation of the Contrast of the SHG Image and the THG Image in AD Brain Tissues To quantitatively understand the correlation of the THG and the SHG signals originating from the Aβ plaques and the NFT, the Pearson's correlation (R) coefficient is used as below:

$$R = \frac{\sum_{i=1}^{n}(X_{THG} - \overline{X}_{THG})(Y_{SHG} - \overline{Y}_{SHG})}{(n-1)S_{THG}Y_{SHG}} \quad \text{(Equation 1)}$$

where $X_{THG}$ and $Y_{SHG}$ are the THG intensity and the SHG intensity respectively, $\overline{X}_{THG}$ and $\overline{Y}_{SHG}$ denote their means while the corresponding standard deviations are $S_{THG}$ and $S_{SHG}$. Before performing the Pearson's correlation coefficient calculations, each raw image was denoised and Otsu's thresholding was performed to make sure the signals were from the THG and the SHG only. To determine the Pearson's correlation coefficient for the Aβ plaques between the THG and the SHG signals, the corresponding region of interest (ROI) for the Aβ plaques in two channels THG and SHG was chosen and compared. Similar procedure was also performed for the NFT. The effect size of the Pearson's correlation coefficient ranging from 0 to 0.3 is usually considered as little or no association, while more than 0.5 as large association. Please refer to FIG. 4(a), which shows the result of comparison of the Pearson's correlation coefficient between THG and SHG. In FIG. 4(a), it can be seen that the average Pearson correlation coefficient differs statistically significantly (p<0.01) between the THG and the SHG signals for the Aβ plaques and the NFT. Each datum point in FIG. 4(a) represents the correlation between the SHG and the THG signals for a single Aβ plaque or NFT. Following Chi-squared goodness-of-fit test, all the data for the Aβ plaques and the NFT have been found to be normally distributed. The calculated mean Pearson's correlation coefficient±standard error of mean (SEM) for the Aβ plaques is 0.76±0.02, while that for the NFT is 0.39±0.02. Therefore, the most Aβ plaques can simultaneously provide contrast for both THG and SHG. However, a weak association between THG and SHG is present for NFT. By treating THG and SHG as the sources of the color addition, this low p-value supports the observation that the final additive colors of the Aβ plaques and the NFT are statistically different. Furthermore, a pixel-by-pixel analysis for the images is also performed to pin point the contrast origin of THG and SHG from the Aβ plaques and the NFT.

Figure 4B:
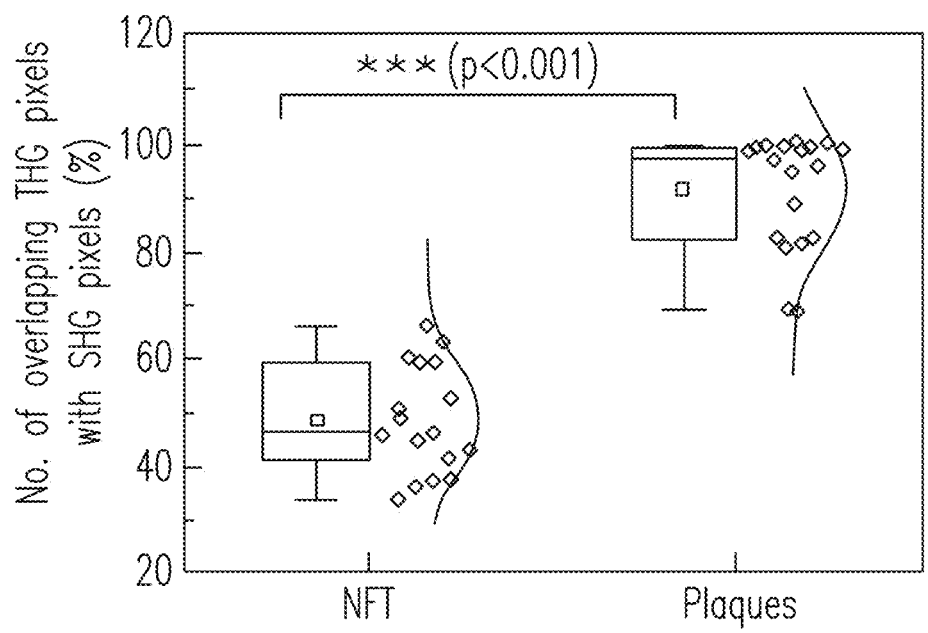
FIG. 4(b) shows the result of the pixel-by-pixel analysis of number of overlapping THG pixels with SHG pixels.

In the pixel-by-pixel analysis, the exact number in percentage of the overlapping THG pixels with SHG pixels is determined. As previously, the analysis was performed after denoising and Otsu's thresholding. Please refer to FIG. 4(b), which shows the result of the pixel-by-pixel analysis. In FIG. 4(b), each datum point represents the overlapping THG pixels with SHG pixels for a single Aβ plaque or NFT. The data is normally distributed. From the result in FIG. 4(b), it can be easily inferred that approximately 91% THG pixels overlapped with SHG pixels for the Aβ plaque, and nearly 48% of the same were observed for the NFT. Therefore, color addition of green (THG) and red (SHG) can provide a distinct yellow color for the Aβ plaque, and predominantly red for the NFT.

Evolution of AD Pathology in Different Aged 3xTg Mice

The evolution of AD pathology in 3xTg mice is observed using the system of the present invention. The brain tissues from the 8 month old 3xTg AD mice are compared with those of the 13 month old 3xTg AD mice, and the images from the system of the present invention are compared with a control C57BL/6 mouse brain slice. The results are shown in FIGS. 5(a)-5(r).

Please refer to FIGS. 5(a)-5(c), which respectively shows the images from the system of the present invention of C57BL/6 mouse brain slice from cortex, striatum and hippocampal layer. In FIGS. 5(a)-5(c), it can be observed that there is no contribution of SHG (with red color) from any structures of the brain, the axons and dendrites appear strongly with green hue of THG, and the cell body of neurons appears as a dark shadow.

The 3xTg mice are widely used as a model system for AD related studies, because the 3xTg mice exhibit plaque and tau pathology which is characteristics of human form. 12 month or older 3xTg mice show plaque and tau pathology in cortical and hippocampus regions of the brain. Accordingly, the system of the present invention is used to image the cortex, striatum and hippocampal layer of the 8 month old 3xTg mouse, and the results are shown in FIGS. 5(d)-5(f) respectively. FIGS. 5(g)-5(i) are enlarged views of the dotted regions respectively in FIGS. 5(d)-5(f). In FIGS. 5(d)-5(f), the cortex, striatum and hippocampal layer showed predominantly THG signals with green hue. However, in FIGS. 5(g)-5(i), very few and small yellow color plaques can be observed in FIG. 5(g) (the arrow region). Moreover, the intracellular red signals can be observed sparsely in the cortex regions and the hippocampal layer, as shown in FIGS. 5(g) and 5(i). Therefore, FIGS. 5(d)-5(i) are considered as the early evolution of NFT and Aβ plaque inside the cell body.

FIGS. 5(j)-5(l) respectively show the images of the system of the present invention of the cortex, striatum and hippocampal layer of the 13 month old 3xTg mouse. FIGS. 5(m)-5(o) are enlarged views of the dotted regions respectively in FIGS. 5(j)-5(l). In FIGS. 5(j)-5(o), the system of the present invention can easily distinguish the Aβ plaques (yellow color), the NFT (red color) and the axons (green color). Therefore, FIGS. 5(j)-5(o) show the intracellular NFT and the Aβ plaque more dominantly as compared to the 8 month old 3xTg mouse, agreeing well with the AD development in 3xTg mouse.

The system of the present invention can also identify flame-like NFT in the cortex of the 13 month old 3xTg mouse. The red color added SHG image, the green color added THG image and the combined image thereof are shown in FIGS. 5(p)-5(r) respectively. In FIGS. 5(p)-5(r), it is confirmed that the flame-like NFT structure can be identified, and it is further confirmed that the presentation the NFT is weaker in the THG image than in the SHG image. Accordingly, in a nut shell, the system of the present invention can visually differentiate different structures of the NFT, Aβ plaques and axons/dendrites.

The gold standard of visualizing the histopathological features of tissues in clinical practice and neuroscience involves staining procedures of fixed tissues, followed by microscopy analysis. Moreover, a multicolor fluorescence imaging also involves exogenous probe to display several structures of brain simultaneously. These kinds of methods are severely time-consuming and most importantly limit the observation of the brain tissues in the native state. Label-free optical imaging techniques can help to improve the situation. The system of the present invention has successfully demonstrated that the additive color multi-harmonic generation microscopy can distinguish different pathological features of AD. The label-free technique can be a potential all-optical virtual biopsy platform for histopathological elucidation of AD brain tissues in clinical perspective. The system of the present invention does not require any pre-processing of the sample, and the sample can be directly utilized under their native state. Using a light source of 1260 nm, THG can provide detailed structural information, such as soma and axonal networks, of the brain tissue with sub-femtoliter resolution. Lipid structures in the axons provide very high contrast for THG. In addition, THG augmented with SHG, can distinguish the two most important pathological hallmarks of AD: Aβ plaques and NFT. Through the Pearson's correlation coefficient estimation between THG and SHG signals, and with pixel-based quantification of overlapping THG pixels with SHG pixels, the present invention shows that the Aβ plaques provide very high contrast for both THG and SHG, and NFT tends to provide more contrast for SHG. The system of the present invention can provide visual display of different pathologies of AD: axons/dendrites as green color, Aβ plaque as yellow color, and NFT as orange/orange-red/apricot color. Moreover, both THG and SHG rely on nonlinear optical excitation phenomenon, and hence, the additive color multi-harmonic generation microscopy can provide natural optical sectional of thick tissue section to provide 3D volumetric images without affecting the viability of the subject. Therefore, the additive color multi-harmonic generation microscopy can hold with the technical value in understanding neuronal networks and AD pathologies at millimeter depths in an intact whole brain.

Materials and Methods

Mice

In the present invention, a wild-type 4 month old C57BL/6 mouse and 4 (one 8 month and three 13 month old) triple transgenic (3xTg) AD mice were used. The results of this experiment primarily focus on demonstrating the capability of the present invention to differentiate AD pathologies through microscopic images. The results do not depend on statistical method to determine the sample size. All the mice were kept on a 12-hour light/12-hour dark cycle and fed ad libitum.

Perfusion and Brain Tissue Slicing

Before the perfusion, the mice were anesthetized with a mixture of 10 mg/kg xylazine (Bayer Vital, Bermany) and 100 mg/kg ketamine (Bela-pharm GmbH & CO. KG, Germany). Using a peristaltic pump, the mice were subsequently perfused transcardially with 0.9% normal saline, followed by 4% paraformaldehyde in 0.1M phosphate-buffered saline (PBS). All the solutions were prepared fresh and kept in ice before perfusion. The brains were removed from the skull and further post-fixed in 4% paraformaldehyde overnight at 4° C. The fixed brains were kept in PBS containing 0.01% sodium azide at 4° C.

Before the brain tissue slicing, the brain was kept submerged in 20% sucrose solution overnight at 4° C. Subsequently, the brain was sectioned coronally using a freezing microtome at a thickness of about 50 μm. These brain tissue slices were first imaged by THG and SHG microscopy, and then, were stained following immunohistochemical procedure for comparison with harmonic generation microscopy images.

Immunohistochemical (IHC) Staining of the Brain Tissues

The immunohistochemical staining of the brain tissue sections were performed following standard protocols. In brief, the tissue sections were first washed in 1× PBS containing 0.1% TritonX-100 (PBST) three times each for 10 minutes. To avoid unspecific binding of the primary antibody, the tissue sections were incubated in blocking buffer (PBST and 5% normal goat serum (NGS)) for 90 minutes on a shaker at room temperature. After blocking, the tissue sections were incubated in primary antibody at 1:1000 in PBST containing 1% NGS overnight at 4° C. Following day, the tissue sections were washed three times (each for 10 minutes) in PBST at room temperature, and were, subsequently, incubated in secondary antibody (Alexa Fluor 594-conjugated goat anti-mouse antibody, Jackson ImmunoResearch, PA, USA) at 1:1000 prepared in 1% NGS/PBST for 120 minutes at room temperature. After washing the tissue sections as before, the brain tissue sections were mounted on poly-L-lysine coated glass coverslips and further used for fluorescence imaging under Leica LSM SP8 confocal microscope (Leica Microsystems, Wetzlar, Germany). The primary antibodies used for staining Aβ-plaques and NFT respectively was anti-β-amyloid produced in mouse (BioLegend, San Diego, USA) and monoclonal anti-PHF1 antibody produced in mouse (Sigma-Aldrich, St. Louis, USA).

Experimental Set Up of the Multi-Harmonic Generation Microscope

Figure 6:
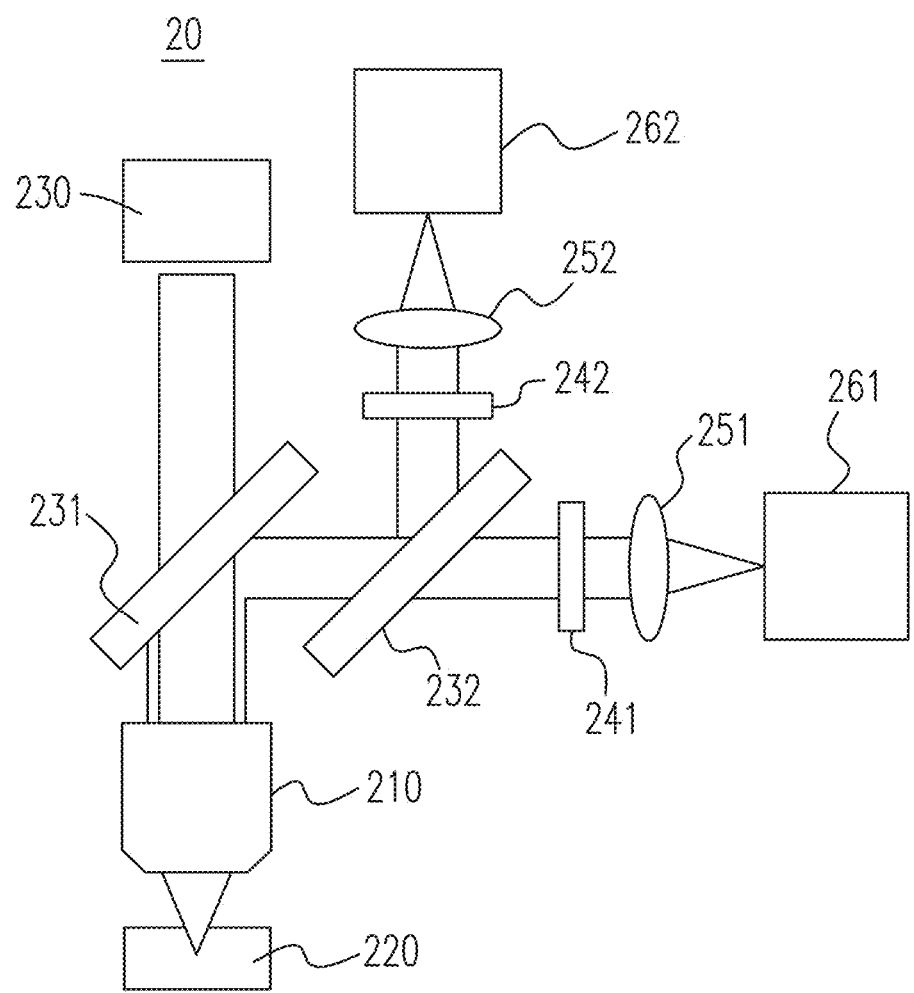
FIG. 6 shows a schematic diagram of multi-harmonic generation microscope of the present invention.

Please refer to FIG. 6, which is a schematic diagram of multi-harmonic generation microscope 20 of the present invention. The harmonic generation excitation source 230 of the present invention was a home-built Cr: Forsterite laser, capable of producing femtosecond pluses (37 fs) with a repetition rate of 105 MHz at central wavelength of 1260 nm (bandwidth: 96 nm). All the experiments were performed on an inverted Olympus microscope IX71 (Olympus, Tokyo, Japan). The dispersion of the optical component for shortening the laser temporal pulsewidth in tissues was compensated by a pair of chirp-mirrors. In the present invention, a galvo-resonant scanning head (MPM-2PKIT) was used for the two-dimensional (2D) scanning of the sample. A scan lens and a tube lens inside IX71 were used to fill the back aperture of a microscope objective. A 40×, 1.15 numerical aperture (NA) water-immersion objective 210 (UAPON 40XW340, Tokyo, Olympus) focused the scanning beam onto the sample 220. For z scanning, the objective 210 was attached to an electronically controllable stage (TSDM40-15X, SIGMA KOKI, Japan). A neutral density (ND) filter was used to control the laser power at the sample focal plane, and an average power of 20-30 mW was maintained to image the samples. The higher harmonic generation signals (SHG and THG signals) were epi-collected by the same objective 210 and focused on photomultiplier tubes (PMT) after reflected by a first dichroic beamsplitter (DM) 231 (FF705-Di01, Semrock, New York, USA). The back-reflection laser lights were blocked by a color filer (CG-KG-5-50, CVI Optics, Albuquerque, USA). In detailed, the SHG and THG signals were separated by a second dichroic beamsplitter 232 (FF705-Di02-25x36, Semrock, N.Y., USA). The SHG signal was further filtered by a first bandpass filter 241 (FF01-618/50, Semrock, N.Y., USA), and amplified by a SHG photomultiplier tube 261 after passing through a first focusing lens 251. The THG signal was further filtered by a second bandpass filter 242 (FF01-417/60, Semrock, N.Y., USA), and amplified by a THG photomultiplier tube 262 after passing through a second focusing lens 252. The SHG and THG signals were recorded and real-time displayed by a commercially available ThorImageLS GUI (ThorImageLS 1.3, Thorlabs). All images were collected with 1024×1024 pixels and 10 image frames were accumulated as one image for a better image quality.

Data Analysis

Free image analysis software, FIJI Image J, was used for display purpose and performing Otsu's thresholding operation. Moreover, standard defined function of MATLAB 2016B were used for Pearson's correlation calculations and pixel-by-pixel analysis. In image acquisitions, and analysis, the present invention only excluded data whose quality was compromised by identifiable reasons, such as flawed sample preparations, and poor signal-to noise ratio. To check the normal distribution of the data set, Chi-square goodness-of-fit test was performed with level of significance 0.05.

Embodiments

1. A system for detecting whether a subject having a target suffers from an Alzheimer's disease, including: a multi-harmonic generation microscope imaging the target by a second harmonic generation (SHG) and a third harmonic generation (THG) to respectively obtain an SHG image and a THG image; and a processor coupled to the multi-harmonic generation microscope and configured to: add a first color to the SHG image and a second color to the THG image to respectively obtain a color-added SHG image and a color-added THG image; and combine the color-added SHG image and the color-added THG image to obtain a combined image, wherein the combined image is used to determine whether the subject suffers from the Alzheimer's disease.

2. The system according to Embodiment 1, wherein the target is a brain tissue.

3. The system according to Embodiment 1 or 2, wherein the processor is further configured to change the first color and the second color to a third color at a portion where the first color overlaps with the second color on the combined image.

4. The system according to any one of Embodiments 1 to 3, wherein the first color having a first color intensity is red, the second color having a second color intensity is green, and the third color is a color falling between red and green.

5. The system according to any one of Embodiments 1 to 4, wherein the color of the third color depends on the first color intensity and the second color intensity.

6. The system according to any one of Embodiments 1 to 5, wherein when the first color intensity and the second color intensity are the same, the third color is yellow, and when the first color intensity is stronger than the second color intensity, the third color is orange.

7. The system according to any one of Embodiments 1 to 6, wherein on the combined image, the green color represents axons and dendrites of a neuron cell, the yellow color represents amyloid-β (Aβ) plaques, and the red color or the orange color represents neurofibrillary tangles (NFT).

8. The system according to any one of Embodiments 1 to 7, wherein when the combined image has the yellow color and at least one of the red color and the orange color, the subject suffers from the Alzheimer's disease.

9. A method for detecting whether a subject having a target suffers from an Alzheimer's disease, including steps of: imaging the target by a second harmonic generation (SHG) and a third harmonic generation (THG) via a multi-harmonic generation microscope to obtain an SHG image and a THG image; adding a first color for the SHG image and a second color for the THG image via a processor to obtain a color-added SHG image and a color-added THG image; combining the color-added SHG image and the color-added THG image via the processor to obtain a combined image; and determining whether the subject suffers from the Alzheimer's disease according to the combined image of the target.

10. The method according to Embodiment 9, further including a step of: changing of the first color and the second color to a third color at a portion where the first color overlaps with the second color on the combined image.

11. The method according to Embodiment 9 or 10, wherein the first color having a first color intensity is red, the second color having a second color intensity is green, and the third color is a color falling between red and green.

12. The method according to any one of Embodiments 9 to 11, wherein the color of the third color depends on the first color intensity and the second color intensity.

13. The method according to any one of Embodiments 9 to 12, wherein when the first color intensity and the second color intensity are the same, the third color is yellow, and when the first color intensity is stronger than the second color intensity, the third color is orange.

14. The method according to any one of Embodiments 9 to 13, wherein on the combined image, the green color represents axons and dendrites of neural cells, the yellow color represents amyloid-β (Aβ) plaques, and the red color, the orange color, or the apricot color represents neurofibrillary tangles (NFT).

15. The method according to any one of Embodiments 9 to 14, further including a step of: determining the subject suffers from the Alzheimer's disease when the combined image has the yellow color and at least one of the red color and the orange color.

16. A method for detecting a characteristic of a neural structure, including: imaging a target by a second harmonic generation (SHG) and a third harmonic generation (THG) via a multi-harmonic generation microscope to obtain an SHG image and a THG image respectively; processing the SHG image and the THG image with two different image processing treatments to obtain a processed SHG image and a processed THG image respectively, wherein a combination of the two different image processing treatments highlights the characteristic; and combining the processed SHG image and the processed THG image to obtain a combined image to determine the characteristic.

17. The method according to Embodiment 16, wherein each of the images processing treatment is a color addition, and after processing the SHG image and the THG image by the two different image processing treatments respectively, the processed SHG image shows a red color, and the processed THG image shows a green color.

18. The method according to Embodiment 16 or 17, further including: at a portion where the red color and the green color overlap on the combined image, changing the red color and the green color to a yellow color.

19. The method according to any one of Embodiments 16 to 18, wherein the green color represents axons and dendrites, the red color represents neurofibrillary tangles (NFT), and the yellow color represents amyloid-β (Aβ) plaques.

20. The method according to any one of Embodiments 16 to 19, wherein the target is a brain tissue of a subject, and the characteristic of the neural structure is used to determine whether the subject suffers from an Alzheimer's disease.

The present invention shows, for the first time, a label-free additive-color multi-harmonic generation microscopy to elucidate, concurrently with different hues, Alzheimer's disease (AD) neuropathological hallmarks: amyloid β (Aβ) plaques and neurofibrillary tangles (NFT). The present invention can differentiate the neuropathological hallmarks of AD by providing different additive colors among Aβ plaques, NFT and neuronal axons. Therefore, the label-free technique of the present invention fulfills the unmet challenge in the clinical histopathology for stain-free slide-free differential visualization of neurodegenerative disease pathologies, with a sub-femtoliter resolution in a single image field-of-view.

Although the present invention has been described with reference to certain exemplary embodiments thereof, it can be understood by those skilled in the art that a variety of modifications and variations may be made to the present invention without departing from the spirit or scope of the present invention defined in the appended claims, and their equivalents.

What is claimed is:

1. A system for detecting whether a subject having a target suffers from an Alzheimer's disease, comprising:
a multi-harmonic generation microscope imaging the target by a second harmonic generation (SHG) and a third harmonic generation (THG) to respectively obtain an SHG image and a THG image; and
a processor coupled to the multi-harmonic generation microscope and configured to:
add a first color to the SHG image and a second color to the THG image to respectively obtain a color-added SHG image and a color-added THG image; and
combine the color-added SHG image and the color-added THG image to obtain a combined image,
wherein the combined image is used to determine whether the subject suffers from the Alzheimer's disease.

2. The system as claimed in claim 1, wherein the target is a brain tissue.

3. The system as claimed in claim 1, wherein the processor is further configured to change the first color and the second color to a third color at a portion where the first color overlaps with the second color on the combined image.

4. The system as claimed in claim 3, wherein the first color having a first color intensity is red, the second color having a second color intensity is green, and the third color is a color falling between red and green.

5. The system as claimed in claim 4, wherein the color of the third color depends on the first color intensity and the second color intensity.

6. The system as claimed in claim 5, wherein when the first color intensity and the second color intensity are the same, the third color is yellow, and when the first color intensity is different from the second color intensity, the third color is orange.

7. The system as claimed in claim 6, wherein on the combined image, the green color represents axons and dendrites of a neuron cell, the yellow color represents amyloid-β (Aβ) plaques, and the red color and/or the orange color represents neurofibrillary tangles (NFT).

8. The system as claimed in claim 7, wherein when the combined image has the yellow color and at least one of the red color and the orange color, the subject suffers from the Alzheimer's disease.

9. A method for detecting whether a subject having a target suffers from an Alzheimer's disease, comprising steps of:
imaging the target by a second harmonic generation (SHG) and a third harmonic generation (THG) via a multi-harmonic generation microscope to obtain an SHG image and a THG image;
adding a first color for the SHG image and a second color for the THG image via a processor to obtain a color-added SHG image and a color-added THG image;
combining the color-added SHG image and the color-added THG image via the processor to obtain a combined image; and
determining whether the subject suffers from the Alzheimer's disease according to the combined image of the target.

10. The method as claimed in claim 9, further comprising a step of:
changing of the first color and the second color to a third color at a portion where the first color overlaps with the second color on the combined image.

11. The method as claimed in claim 10, wherein the first color having a first color intensity is red, the second color having a second color intensity is green, and the third color is a color falling between red and green.

12. The method as claimed in claim 11, wherein the color of the third color depends on the first color intensity and the second color intensity.

13. The method as claimed in claim 12, wherein when the first color intensity and the second color intensity are the same, the third color is yellow, and when the first color intensity is different from the second color intensity, the third color is orange.

14. The method as claimed in claim 13, wherein on the combined image, the green color represents axons and dendrites of neural cells, the yellow color represents amyloid-β (Aβ) plaques, and the red color or the orange color represents neurofibrillary tangles (NFT).

15. The method as claimed in claim 14, further comprising a step of:
determining the subject suffers from the Alzheimer's disease when the combined image has the yellow color and at least one of the red color and the orange color.

16. A method for detecting a characteristic of a neural structure, comprising:
imaging a target by a second harmonic generation (SHG) and a third harmonic generation (THG) via a multi-harmonic generation microscope to obtain an SHG image and a THG image respectively;
processing the SHG image and the THG image with two different image processing treatments to obtain a processed SHG image and a processed THG image respectively, wherein a combination of the two different image processing treatments highlights the characteristic; and
combining the processed SHG image and the processed THG image to obtain a combined image to determine the characteristic.

17. The method as claimed in claim 16, wherein each of the images processing treatment is a color addition, and after processing the SHG image and the THG image by the two different image processing treatments respectively, the processed SHG image shows a red color, and the processed THG image shows a green color.

18. The method as claimed in claim 17, further comprising:
at a portion where the red color and the green color overlap on the combined image, changing the red color and the green color to a yellow color.

19. The method as claimed in claim 18, wherein the green color represents axons and dendrites, the red color represents neurofibrillary tangles (NFT), and the yellow color represents amyloid-β (Aβ) plaques.

20. The method as claimed in claim 16, wherein the target is a brain tissue of a subject, and the characteristic of the neural structure is used to determine whether the subject suffers from an Alzheimer's disease.

* * * * *